United States Patent [19]

Martinetti

[11] Patent Number: 4,654,214

[45] Date of Patent: Mar. 31, 1987

[54] METHOD OF TREATING RESPIRATORY DISEASE IN ANIMALS

[76] Inventor: Patrick J. Martinetti, R.D. 1, Box 161, Cochecton, N.Y. 12726

[21] Appl. No.: 694,002

[22] Filed: Jan. 23, 1985

[51] Int. Cl.$^4$ .............................................. A61K 35/78
[52] U.S. Cl. .................................. 424/195.1; 514/849
[58] Field of Search ..................... 424/195.1; 514/849

[56] References Cited

PUBLICATIONS

The Merck Manual, p. 532, 1972.
Steinmetz, Codex Vegetabilis, 1957, No. 965.
Lewis, Medical Botany 1977, p. 389.

*Primary Examiner*—Donald B. Moyer
*Assistant Examiner*—John W. Rollins, Jr.
*Attorney, Agent, or Firm*—Prutzman, Kalb, Chilton & Alix

[57] ABSTRACT

The symptoms of chronic alveolar emphysema in horses are palliated by daily feeding the effected horses a handful of the red berries from the staghorn sumac for a period of at least about two weeks.

6 Claims, No Drawings

METHOD OF TREATING RESPIRATORY DISEASE IN ANIMALS

BACKGROUND AND SUMMARY OF THE INVENTION

The present invention relates generally to the treatment of chronic respiratory diseases in animals and is more particularly concerned with a new and improved method for treating such diseases, particularly in horses.

A common respiratory ailment of horses is a form of pulmonary emphysema known as chronic alveolar emphysema. Although emphysema has been known to affect the lungs of a variety of animals, such as cows, pigs, sheep, dogs and cats, the alveolar emphysema form is of significance primarily in horses and is referred to colloquially by the outdated expressions "broken wind" or "heaves." This type of disease results in abnormal enlargement of the air spaces distal to the terminal bronchioles with evidence of destruction of the wall tissue. The disease is categorized in horses by labored expiration; i.e., difficultly in forcing air out of the lungs, frequently featured by a double expiratory effort, by chronic cough, unthriftiness and lack of stamina. The cause of this form of emphysema is not known but it is known that the condition is often associated with over work and/or the ingestion of musty, damaged or dust-laden feed. Some types of the disease appear as after effects of pneumonia or appear to be a pulmonary allergic reaction to certain grains, especially oats. The disease is usually progressive and in advanced cases the expiratory phase of the respiratory cycle is prolonged with forced contractions of the chest and abdominal muscles resulting in the formation of ridges or heave lines beneath the posterior of the rib cage and with the animal having the appearance of an enlarged chest cavity. Other symptoms include short, weak, persistent, dry coughing, audible wheezing, and nasal discharge with the nostrils often slightly dilated.

No specific cure is known for the respiratory ailment and heretofore the only treatment has been the use of corticosteroids and other drugs coupled with the use of feed free from dust, frequently in a pelleted form. Further the animal should be kept on a green pasture and can be used only for light work.

It is an object of the present invention to provide a new and improved method of treating chronic respiratory disease in animals through the use of an extremely simple yet highly effective treatment that substantially palliates the symptons mentioned hereinbefore.

A further object of the present invention is to provide a method of the type described that utilizes natural substances and is readily combined with the normal feeding routine of the animal.

Another object of the present invention is to provide a technique that is facile, of relatively low cost, effective within only a few weeks of treatment and is long lasting.

Other objects and advantages will be in part obvious and in part pointed out more in detail hereinafter.

These and related features are achieved in accordance with the present invention by providing a method of treating animals suffering from emphysema with the fruit from certain plant species of the genus Rhus, also referred to as sumac.

A better understanding of the invention will be obtained from the following description of the method including the steps thereof and the relation of one or more steps with respect to each of the others as well as the features, characteristics, properties and relationships described and exemplified herein.

DESCRIPTION OF THE PREFERRED EMBODIMENT

As mentioned, it has now been found in accordance with the present invention that the symptoms of chronic alveolar emphysema can be palliated if the effected animal is fed, either separately or in admixture with its feed ration, the naturally occurring fruit from a plant of the genus Rhus. This fruit typically takes the form of red or crimson berry clusters that can be gathered easily and hand fed to the animal or mixed with the animals basal feed ration. Typically, administration of the treatment approximately every day for a period of about two weeks to one month has proven effective in most instances although more prolonged treatment may be required for severe cases.

The plant genus Rhus is of the anacardiaceae family which has about 150 different species native to the temperate and subtropical regions of both hemispheres. Some of the species of the genus Rhus are extremely poisonous and include those plants commonly referred to poison ivy, poison oak and poison sumac. All of these poisonous species bear fruit that exhibit a white to greyish coloration and although they do not adversely affect birds, have not been tested for use in accordance with the present invention.

The nonpoisonous fruit varieties utilized in accordance with the present invention are brightly red to reddish brown or crimson in coloration. Dilute aqueous infusions or extracts of these berries have been utilized heretofore in herbal medicinal formulations. For example, infusions of the fruit are alleged to have been regularly taken for diabetes, gargled for quinsy and ulcers of the throat and used as a wash for ulcers, running tetters, ringworm and other foul skin diseases. It has also been said that powders made from the fruit are effectively used to coagulate the blood and stop hemorrhaging. The powdered berries also have been made into ointments said to be effective in healing scratches, cuts, and wounds, and for treating infection, burns, scalds and even various skin diseases or sores that become infected including eczema, shingles and numerous viral ailments. Its most extensive use, however, appears to be in the form of infusions utilized as a gargle for sore throats and in the treatment of colds and flu. In this connection, reference may be had to U.S. Pat. No. 43,128 issued to Frank Norton in 1864.

In accordance with the present invention, various plant species of the genus Rhus may be efficaciously employed. However, the preferred material are the fruit or berries from the more commonly occurring edible species of this plant genus; namely, *Rhus typhina* (staghorn sumac) and *Rhus glabra* (smooth or scarlet sumac). Other varieties believed to be effective include *Rhus copallina* (winged sumac), *Rhus aromatica* (fragrant sumac), *Rhus trilobata* (squaw bush or ill-scented sumac) and *Rhus integrifolia* (sour berry tree). Additionally, European varieties such as *Rhus cotinus* (wig or smoke tree) and *Rhus coriaria* (Sicilian sumac) may also be employed.

The preferred *Rhus typhina* is characterized by small, crimson-haired berries that appear on the plant in early autumn in the form of compact fruit bunches made up of small single-seeded berry-like drupes. The startling crimson berries are covered with bright scarlet hairs pleasantly sharp to the taste with malic acid, which is the same substance that flavors grapes. The fruit of the *Rhus glabra* is typically a more brightly reddish color with significantly smaller hairs of only about 0.2 millimeters in length as contrasted with the slender tapering hairs of 1-2 millimeter length possessed by the fruit of the *Rhus typhina*.

In view of the plentiful nature of the plants, it is possible to gather the fruit therefrom easily and either feed it directly to the horses effected by alveolar emphysema or admix the fruit with the normal feed of the horse, such as merely by placing a handful of the fruit into and admixing it with the horses basic feed allocation.

Since the material being administered to the animal is a natural substance known to be edible, the exact amount used need not be measured with precision. In this connnection it has been found that about one or two handfuls of berries with each daily feeding has proved effective. The treatment usually is maintained for at least about two weeks up to about one to two months although no harmfull effects have been noted where a longer treatment time is used.

In order that the present invention may be more readily understood, reference will be made to the following examples which are by given for the purpose of illustration only and are not intended to in any way limit the pratice of the invention.

The method of the present invention has been employed with excellent results in connection with the treatment of at least a dozen horses of varying age and condition. For example, a twenty-eight year old registered standard bred mare was treated by directly feeding it handfuls of the berries from the plant *Rhus typhina* on a daily basis over a period of several months. Prior to the treatment, the horse had been suffering from emphysema. For the past three years since treatment the animal has exhibited none of the symptoms of emphysema.

A thirty-year old grey gelding was similarly treated for a period of about one month and following treatment showed no evidence of emphysema for a period of two years. A twenty-five year old chestnut mare developed heaves in 1980 and was treated for a period of two weeks in August 1981. The horse has exhibited only very slight symptoms of emphysema to date. An eight-year old chestnut mare walking horse diagnosed as having emphysema was treated for about one month and showed no signs of emphysema eight months later when it was sold. Similarly, a fourteen-year old gray mare was treated for two weeks and showed no signs of emphysema when sold five months later.

An eight-year old calico point pony gelding suffering from emphysema was treated for a period of about one month and showed no evidence of emphysema when sold eighteen months after treatment.

Similar results have been evidenced in treating a twelve-year old bay gelding for two weeks, a ten-year Appaloosa gelding as well as by a recently treated eight-year old gelding. A seventeen-year old sorrel mare diagnosed as having severe alveolar emphysema was treated for a two-week period and exhibited only very slight symptoms six months later.

As will be apparent to persons skilled in the art, various modifications, adaptations and variations of the foregoing specific disclosure can be made without departing from the teachings of the present invention.

What is claimed is:

1. A method of treating chronic respiratory disease of the alveolar emphysema type in an animal comprising orally administering to an animal suffering from the disease an amount of at least one hand full of the crimson fruit from a plant of the genus Rhus to provide relief from the symptoms of said disease.

2. The method of claim 1 wherein the fruit is admixed with the feed of the animal.

3. The method of claim 1 wherein the fruit is from a plant species selected from the group consisting of *Rhus typhina* and *Rhus glabra*.

4. The method of claim 3 wherein the crimson fruit is from the plant species *Rhus typhina*.

5. The method of claim 3 wherein the fruit is from the plant species *Rhus glabra*.

6. A feed composition well-suited for horses believed to have chronic alveolar emphysema comprising a basal feed ration and of at least one hand full of the crimson fruit from a plant of the genus Rhus, said amount being sufficient to provide relief from the symptoms of said emphysema.

* * * * *